United States Patent [19]
Salmon et al.

[11] Patent Number: 5,898,817
[45] Date of Patent: Apr. 27, 1999

[54] INFANT WARMER WITH HEIGHT ADJUSTMENT MECHANISM

[75] Inventors: Andrew Paul Maxwell Salmon; Christopher Peter Hutchinson, both of Auckland, New Zealand

[73] Assignee: Fisher & Paykel Limited, Auckland, New Zealand

[21] Appl. No.: 08/801,822

[22] Filed: Feb. 14, 1997

[51] Int. Cl.$^6$ .................................................. A61G 11/00
[52] U.S. Cl. ........................... 392/418; 219/521; 600/22; 5/11; 108/145
[58] Field of Search ................................... 392/418, 411, 392/412, 415; 219/521, 385; 600/22; 5/11; 108/144.11, 145; 248/669, 161, 157, 178.1, 188.2

[56] References Cited

U.S. PATENT DOCUMENTS

| | | | |
|---|---|---|---|
| 2,652,574 | 9/1953 | Toomey | 5/11 |
| 3,220,020 | 11/1965 | Nelson | 5/11 |
| 3,646,319 | 2/1972 | Auld . | |
| 3,858,570 | 1/1975 | Beld et al. | 600/22 |
| 4,221,211 | 9/1980 | Brasch | 600/22 |
| 4,628,553 | 12/1986 | Buttitta et al. | 248/161 |
| 4,682,810 | 7/1987 | Zarka | 296/20 |
| 4,809,677 | 3/1989 | Mackin et al. | 600/22 |
| 4,885,918 | 12/1989 | Vaccaro | 600/22 |
| 5,162,038 | 11/1992 | Wilker | 600/22 |
| 5,418,987 | 5/1995 | Yoshino | 5/11 |
| 5,453,077 | 9/1995 | Donnelly et al. | 600/22 |
| 5,498,229 | 3/1996 | Barsky et al. | 600/22 |
| 5,624,375 | 4/1997 | Dykes et al. | 600/22 |

FOREIGN PATENT DOCUMENTS

| | | | |
|---|---|---|---|
| 619995 | 10/1994 | European Pat. Off. | 392/418 |
| 218449 | 3/1909 | Germany | 5/11 |
| 1114290 | 9/1961 | Germany | 108/145 |
| 3544301 | 6/1987 | Germany . | |
| 9-206344 | 8/1997 | Japan . | |
| 120572 | 1/1948 | Sweden | 5/11 |
| 8304168 | 12/1983 | WIPO | 5/11 |

*Primary Examiner*—John A. Jeffery
*Attorney, Agent, or Firm*—Trexler, Bushnell, Giangiorgi & Blackstone, Ltd.

[57] ABSTRACT

An infant warmer for use in a Healthcare environment for the examination and treatment of newborn babies. A column supports an infra-red radiant heater above a support surface on which the baby is positioned. The support source is cantilevered from the column. The column is carried by a base section which is provided with wheels to allow the infant warmer to be easily transported. The base section includes an automated height adjustment mechanism which allows a user to easily adjust the height of the support surface by raising; or lowering the column. The infant warmer is made in a modular fashion to be easily customised for any particular environment or special requirement by constructing the column from a "U" shaped extrusion which allows various Healthcare modules to be inserted as required to suit particular requirements.

17 Claims, 4 Drawing Sheets

INFANT WARMER WITH HEIGHT ADJUSTMENT MECHANISM

FIELD OF THE INVENTION

This invention relates to height adjustment mechanisms and modular construction techniques, and more particularly though not solely to automated height adjustment mechanisms and modular construction techniques used in the construction of infant warmers.

DESCRIPTION OF THE PRIOR ART

In comparison to an incubator, an infant warmer has the advantage that it is an open care bed and accordingly easy access to the infant (for example by medical staff) is readily available, whereas an incubator is a closed care bed where the infant is sealed from the ambient surroundings. As a result, infant warmers are an increasingly accepted component of a new born infant's medical environment where immediate and unlimited access to the infant is often required.

An example of an early infant warmer is disclosed in U.S. Pat. No. 3,646,319 which issued in 1972 and was assigned to Merco Products Inc. The infant warmer disclosed has no height adjustment mechanism for the infant support surface (on which the infant is positioned) and so some medical staff would likely find the height of this warmer uncomfortable or awkward to work with. An example of a medical stretcher having a height adjustment mechanism wherein the two pairs of legs at either end of the bed are pivoted is disclosed in U.S. Pat. No. 4,682,810 issued in 1987 and assigned to Contact Securite—Society d'Exploitation. However, the height adjustment mechanism disclosed requires manual operation, is not optimally stable and would not be suitable in an infant warmer.

More recent examples of infant warmers are disclosed in U.S. Pat. No. 4,809,677 issued to Mackin et al and assigned to the BOC Group PLC Inc., U.S. Pat. No. 5,162,038 issued to Wilker and assigned to Hill-Rom Company and U.S. Pat. No. 5,453,077 issued to Donnelly et al and assigned to Hill-Rom Company Inc. Each of these warmers have a similar construction where the infant support surface is positioned atop a large pedestal. The pedestal is ordinarily considered as wasted space and utilised as a storage area by incorporating drawers therein. The presence of the pedestal below the bed, for example, impedes the use of modem X-ray equipment which could otherwise be positioned beneath the infant support surface so that the infant would not need to be disturbed and removed from the infant warmer for an X-ray.

The above mentioned U.S. Pat. No. 5,453,077 includes an elaborate and complex piston and cylinder arrangement beneath die infant support surface. Accordingly, there is a need for a simple yet effective height adjustment mechanism for use in an infant warmer or the like.

SUMMARY OF THE INVENTION

It is, therefore, an object of the present invention to provide an infant warmer which will go at least some way towards overcoming one or more of the above disadvantages or which will at least provide the public with a useful choice.

Accordingly, in one aspect, the invention consists in a height adjustment mechanism comprising:

a base member having at least two support ends and a principle axis, said principal axis in use adapted to lie in a substantially horizontal plane, at least one leg member having a base attachment end pivotally connected to each said support end of said base member to support said base member above a support surface, each said leg member being rotatable about its connection with said base member in a direction having a component substantially perpendicular to said principal plane of said base member, and having at an end of said leg member away from said base member a supporting foot means supported by and moveable on said support surface, and actuating means operable to rotate each said leg member about its connection with said base member such that the angle of rotation between said leg member and said base member may be adjusted by the actuating means thereby adjusting the height of said base member above said support surface.

In a further aspect, the invention consists in an infant warmer comprising:

a base member having at least two support ends and a principle plane, said principle plane in use adapted to lie in a substantially horizontal plane, a columnar support member connected to said base member and extending substantially perpendicularly therefrom, an infant support structure connected to said columnar support, and a radiant energy source mounted above and adapted to direct radiant energy toward said infant support surface, said radiant energy source connected to said columnar support.

The invention consists in die foregoing and also envisages constructions of which the following gives examples.

DESCRIPTION OF THE DRAWINGS

One preferred form of the present invention will now be described with reference to the accompanying drawings in which.

DETAILED DESCRIPTION OF THE PREFERRED EMBODIMENT

Figure 1:
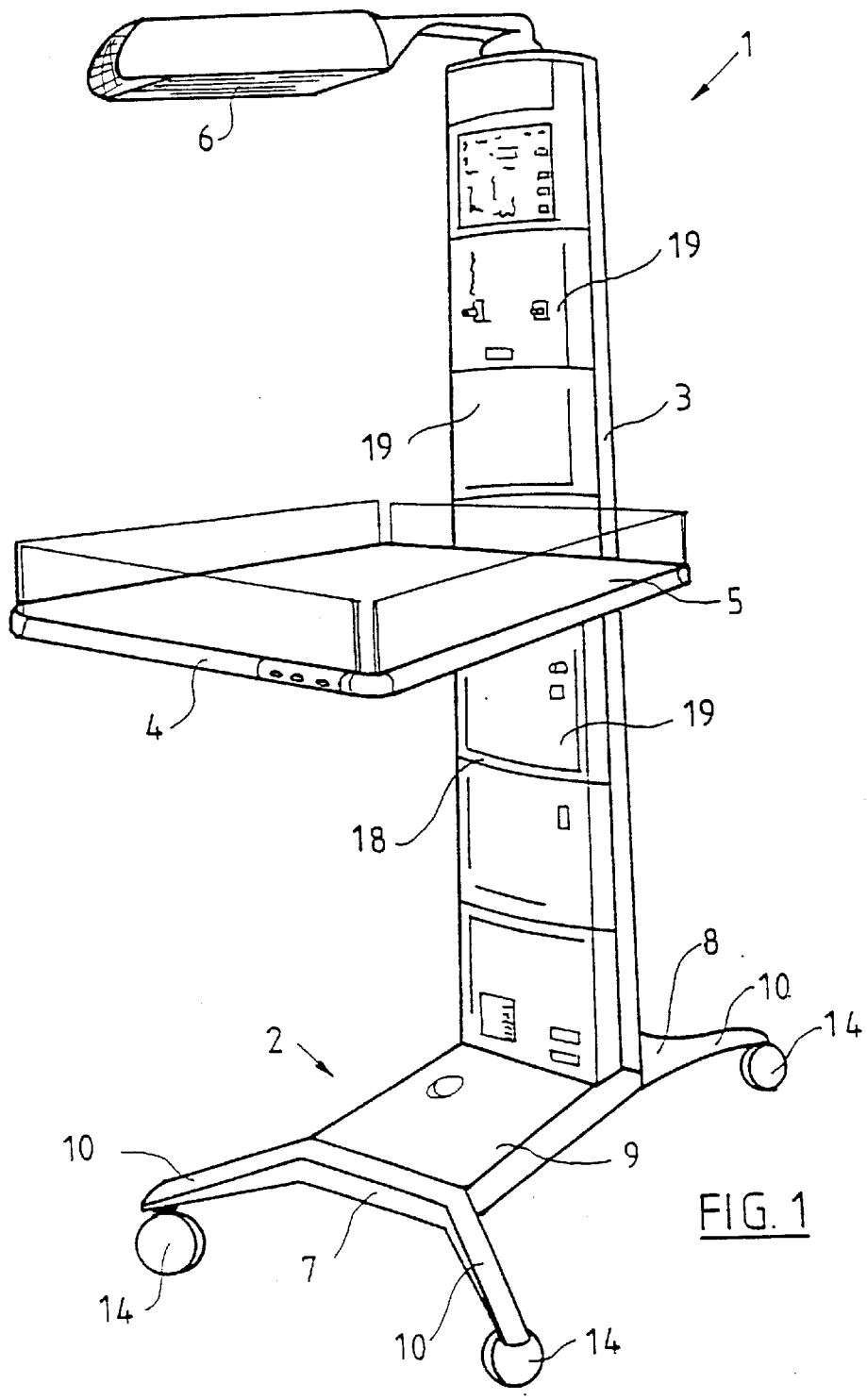
FIG. 1 is a perspective view of an infant warmer according to a preferred form of the present invention.

With reference to the drawings and particularly FIG. 1, an infant warmer 1 is shown having a height adjustment mechanism in accordance with a preferred embodiment of the present invention. It can be seen that the infant warmer 1 has a substantially horizontal, in use, base section 2 carrying a substantially vertical in use support column 3 from which other parts of the infant warmer are supported. Support column 3 supports, for example, a mattress support structure 4 on which a mattress is positioned to carry an infant or baby. A heat source, such as a radiant heat source or heater 6 also protrudes from column 3 and directs heat at the mattress on which the infant or baby will be positioned. A suitable radiant heat source is disclosed in our co-pending New Zealand patent application number 272577. The side elevation of infant warmer 1 resembles an "E" shape.

Figure 6:
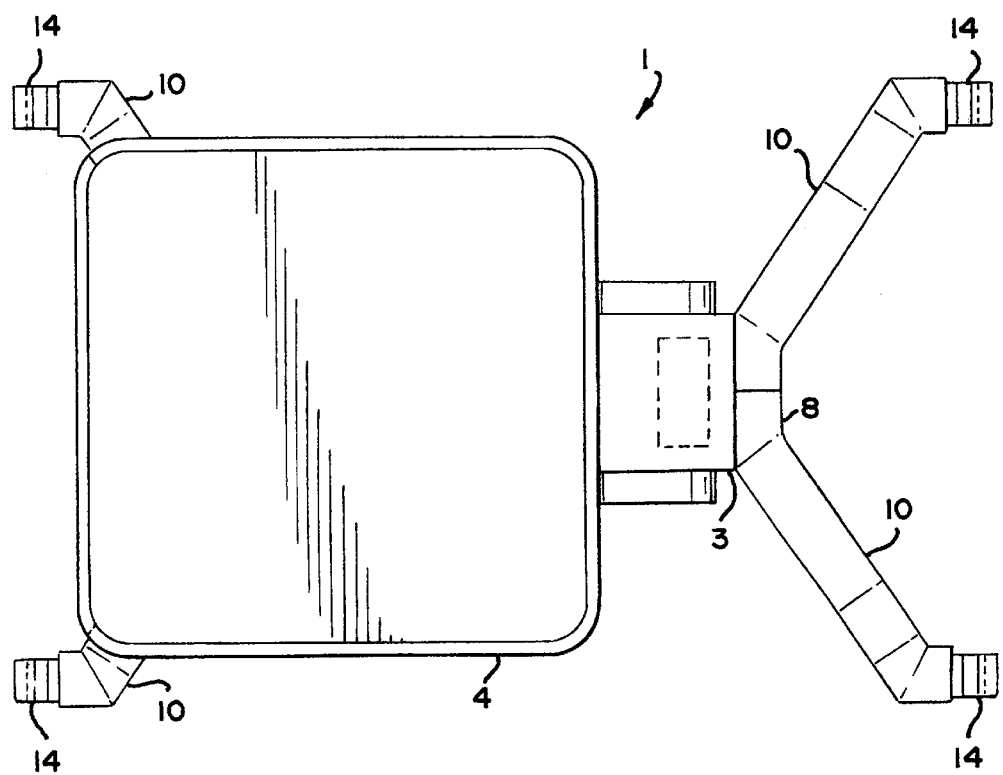
FIG. 6 is a plan view in cross section through B—B of the support column of the infant warmer shown in FIG. 5.

Support column 3 includes a "U" shaped extrusion having an open side and a cover 18 which encloses the open side to form a rigid box section column having a substantially vertical hollow space therein. This may best be seen in FIG. 6. The cover 18 is made up of one or more vertically adjacent sections, each section being either a blank section, the purpose of which is simply to enclose and provide structural rigidity, or a system module 19. The space may be used to accommodate wiring necessary for operation of electrical components of the warmer such as the radiant heater 6. The space also serves to accommodate the operative hardware of the various modules 19 which may be fitted to the "U" shaped extrusion, with any module controls, and indicative displays or readouts presented on the front panel section. The modules 19 may include such features as:

humidification module phototherapy module resuscitation module radiant heater control module temperature controller module, etc The positioning of the modules within the support column will allow easier connection of common services to a number of modules, such as power which may be "daisy chained" to each module in turn, or alternatively, the various modules could connect to bus bars provided vertically within the space of the column. In its most preferred form this would allow modules to automatically contact with the bus bars upon being inserted into the column.

From the foregoing explanation of the "modular construction" of the preferred form of infant warmer it can be seen that the present warmer readily enables customisation of the warmer for a specific customer or patient as well as allowing later "add-on" modules to be incorporated with ease. In addition, the simple yet practical and strong construction having a columnar "backbone" with other dependent structures such as the infant support bed and the radiant heater cantilevered or otherwise suspended therefrom.

In respect of the infant support bed and the radiant heater it is envisaged that these may be constructed as modules which slot into the columnar structure for convenience of manufacture.

Figure 2:
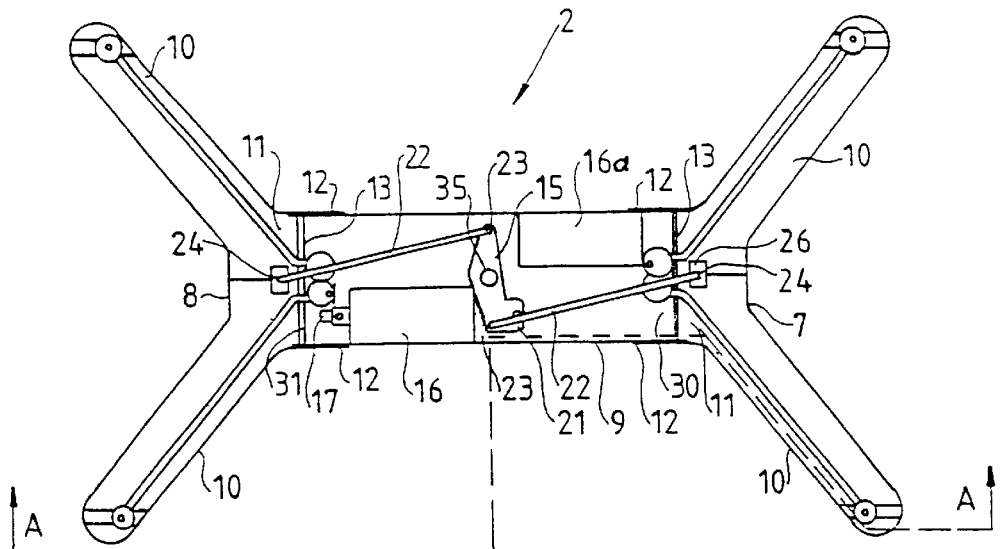
FIG. 2 is a plan view from below of the base section of the infant warmer of FIG. 1 incorporating a height adjustment mechanism according to one aspect of the present invention.
Figure 3:
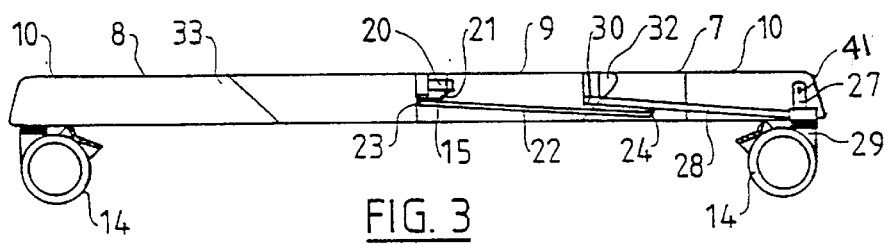
FIG. 3 is a side elevation in partial cross section (through A—A) of the base section of FIG. 2 in a lowered position.
Figure 4:
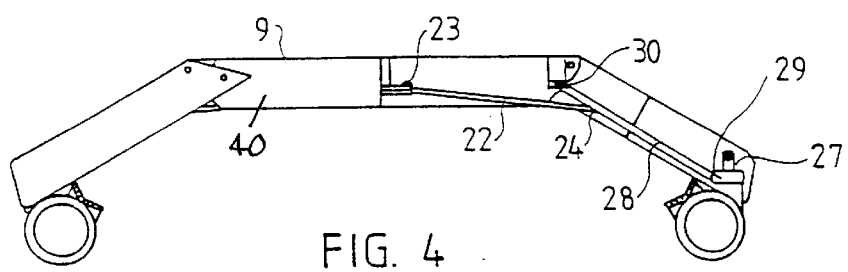
FIG. 4 is a side elevation in partial cross section (through A—A) of the base section of FIG. 2 in a raised position.

Referring to FIGS. 2 to 4 the infant warmer base section 2 includes a base member 9. First and second leg members 7 and 8 extend from opposite ends 30 and 31 of the base member 9 and are pivotable about axes 32 and 33 perpendicular to the principal axis of the base member 9. The leg members 7 and 8 include overlapping flanges 12 which overlap the side flanges 40 of the base member 9. Pivot rods 13 pass through the overlapping flanges and the side walls at the axis of rotation 32 and 33 rotatably connecting the leg members 7 and 8 and the base member 9. For stability the leg members are each configured as a "V" shape, having a pair of branch members 10 which diverge as they extend away from the attachment portion 11 of the leg members 7 and 8 however single legs could conceivably be attached to base member 9. Wheels 14 are provided at the distal ends of the branch members 10. The wheels are generally in the form of free pivoting casters with at least two casters incorporating locking mechanisms. This allows ease of manoeuvring of the equipment while allowing the equipment to be safely located once correctly positioned. The base member and the leg members may be moulded from plastic and have an open underside incorporating reinforcing ribs as necessary. Base section 2 has a "principle axis" which extends along its length, from one leg member 7 to the other leg member 8. In FIG. 1 the principle axis is in the horizontal plane.

A rotatable control member 15 is centrally located under the base member 9 and is rotatable about an axis 35 perpendicular to the principal plane of the base member. This member could take the form of a pulley or other member, but in the illustrated embodiment is a simple dual crank. An electric linear actuator 16 fixed to supporting bracket 17 has its actuation member 20 connected to an extended lug 21 from the control member. The linear actuator 16 is driven by control circuits on circuit board 16A. Extension or retraction of the linear actuator member 20 causes rotation of the control member 15. Other manners of controlling the position of the control member 15 are possible, for example a foot pump operated pneumatic actuator, or a direct rotational drive such as a worm drive gearbox. The electric linear actuator has the advantage of being easily driveable, with a slow steady progression, while also being difficult to force due to its worm drive action. Thus forces on the control member are unlikely to affect its position.

For each leg member an actuation strut 22 extends between the rotatable control member and the leg member. The actuation strut 22 connects at one end to a point 23 on the control member away from the axis of rotation of the control member, and at its other end to a point 24 on its respective leg member. Rotation of the control member therefore effects extension or retraction of the actuation struts relative to the axis of rotation of the respective leg about the base member 9.

The connection points 23 on the control member, and the configuration of the control member have the actuation struts acting with maximum leverage around the rotation axis of the control member. This gives the actuation struts a high travel for small rotations of the control member. The connection points 23 and 24 are configured so that the line of force between the two connection points 23 and 24 of the actuation strut passes at a distance below the rotation axis of the leg member about the base member 9. In the illustrated embodiment the control member is disposed well below the rotation axis, and the actuation strut connects to a plate 26 on the leg, which is fixed to the lower side of the leg. This gives the actuation strut a substantial lever about this rotation axis.

From the above it is clear that rotation of the control member 15, effected by extension of the electric linear actuator, can cause either extension or retraction of the actuation 16 struts, which in turn causes the leg members to rotate about the axis, and the subsequent raising or lowering of the distal ends of the branch members 10, consequently raising or lowering the base member 9 with reference to a support surface on which the infant warmer 1 is supported.

To ensure that the base member 9 remains level, the ratio of the lever of each actuation strut 22 about the axis of rotation of the control member 15 and the lever of the same actuation strut about the rotation axis of its respective leg about the base member 2 is equal across all leg members. In the embodiment shown this is by use of symmetry between legs, however this can also be achieved without symmetry. The above described embodiment for simplicity has only actuated legs. It would however be possible to construct the height adjustment mechanism in an equivalent manner to accommodate more legs, however little advantage would result from the use of more legs.

The wheels of the infant warmer base 2 are configured to remain in consistent vertical alignment. Each wheel is mounted on a wheel pedestal member 27 which is pivotally connected to the underside of the respective branch member adjacent the distal end thereof, about an axis 41 parallel to the axis 32 or 33 of rotation of the leg about the base member. A tie member 28 is connected between a point 29 on the pivotal member and a point 30 on the base member 9. The points 30 and 29 are preferably configured such that the component of the line there between perpendicular to the rotation axis of the respective leg, is parallel to and of equal length to similar component of the line between the pivotal connection point 41 of the wheel pedestal and the rotation axis, or at least is as close as circumstances allow. In the illustrated embodiment the connection point 30 on the base member is made on a raised bracket that is adjacent the end 30 or 31 of the base member.

Figure 5:
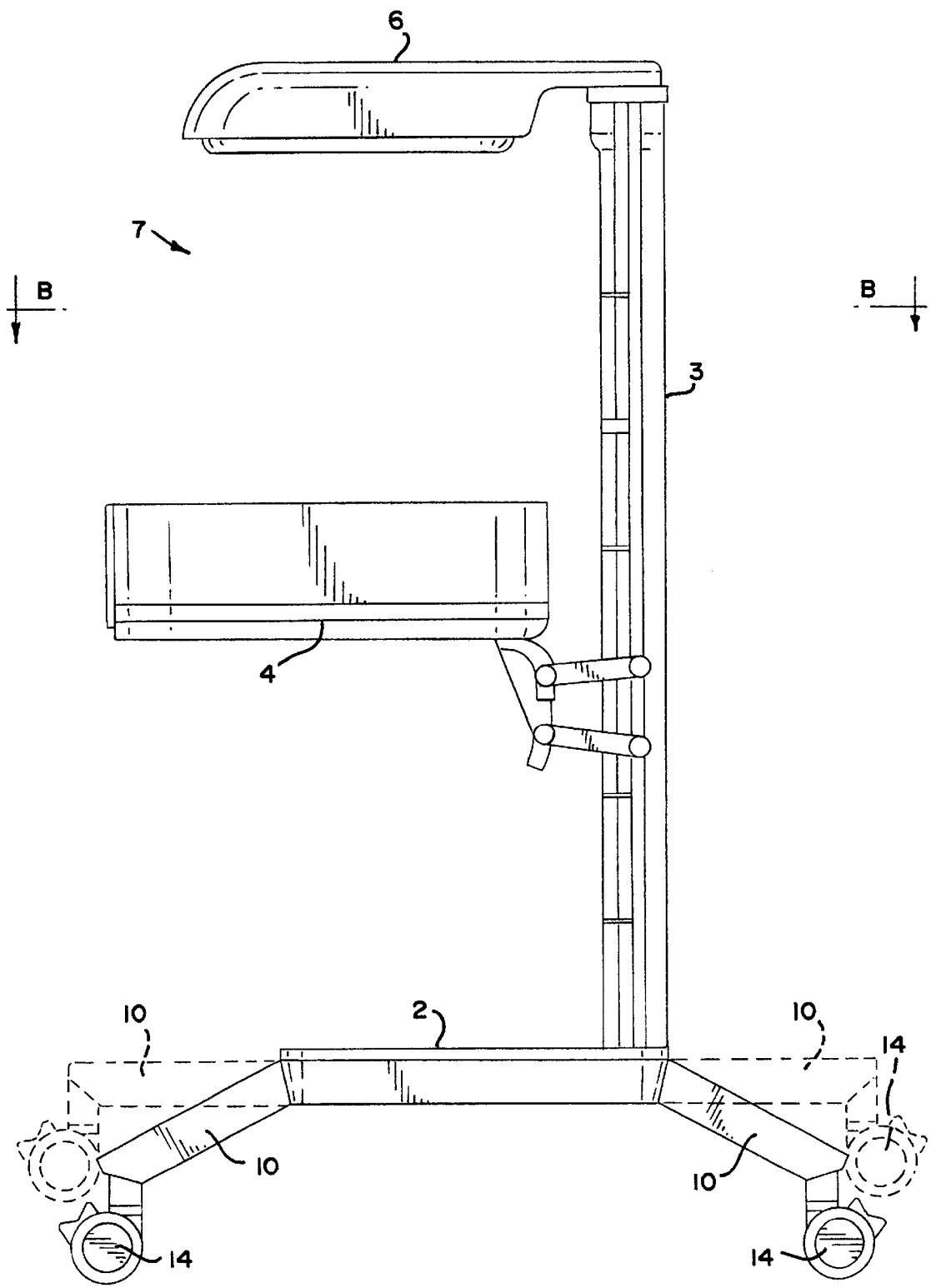
FIG. 5 is a side elevation of the infant warmer of FIG. 1 showing the height adjustment mechanism in both raised (dotted lines) and lowered positions.

Control of the height adjustment mechanism as above described is effected by user manipulation of a control panel. FIG. 5 shows the height adjustment mechanism of the infant warmer according to the present invention, firstly in a raised position (solid lines) and secondly in a lowered position (dotted lines). It can be seen that when the height adjustment mechanism is in a raised position the infant warmer including base section 2, support structure 4 and radiant heat source 6 are actually lowered (closer to the floor) than when in the lowered position.

It is readily apparent that the described adjustment system provides a stable base for the infant warmer, along with easy and accurate height control. The base member is maintained at a level attitude while simply resting and also during operation of the adjustment mechanism. The operation of the mechanism occurs in a smooth, quiet and uninterrupted motion and once halted will retain its position without requiring locking in place. The locking castor wheels under the base remain in approximately constant vertical alignment, facilitating operation of their locking mechanisms.

It can also be readily seen that the adjustment mechanism is well suited to other applications, beyond just infant warmers. The embodiment as described is readily adaptable to any columnar or pedestal type, where medium displacement height adjustment is desirable, particularly wheeled apparatus. Given the quiet, smooth nature of its operation and the ease of its use the equipment is ideally suited to hospital applications.

We claim:

1. A height adjustment mechanism comprising:

a base member having at least two support ends and a principal axis, said principal axis in use adapted to lie in a substantially horizontal plane, at least one leg member, each said leg member pivotally connected to a respective support end of said base member at a base attachment end of said leg member, to support said base member above a support surface, each said leg member being rotatable about its connection with said base member in a direction having a component substantially perpendicular to said principal axis of said base member, and having at an end of said leg member away from said base member a supporting foot means supported by and moveable on said support surface, said at least one leg member having at least two branch segments which form a substantially "V" shape wherein the proximal ends of said branch segments are joined together and the distal ends are apart to provide a measure of lateral stability and wherein each distal end is provided with wheel means, and actuating means operable to rotate each said leg member about its connection with said base member such that the angle of rotation between said leg member and said base member may be adjusted by the actuating means thereby adjusting the height of said base member above said support surface.

2. A height adjustment mechanism as claimed in claim 1 wherein said actuating means comprise a rotatable control member, and for each said leg member an actuation arm means connected at one end thereof to said rotatable control means at a point thereon away from the axis of rotation, and at the other end thereof to said leg member at a point thereon away from the axis of rotation of said leg member about said base member, so that rotation of said control member causes extension or retraction of said actuation arm relative to the rotation axis of said leg member about said base member, thereby causing rotation of said leg members about their connections with said base member.

3. A height adjustment mechanism as claimed in claim 2 wherein the ratio of the lever of said actuation arm means about the axis of rotation of said control member to the lever of said actuation arm means about the axis of rotation of its respective leg member about said base member are constant between said leg members.

4. A height adjustment mechanism as claimed in claim 1 wherein a wheel pedestal member is pivotally connected to the underside of each said branch member, said wheel means are provided on said wheel pedestal member and a tie member is connected at one end to a point on said pedestal member away from the axis of rotation thereof about said leg member and at its other end to a point on said base member, such that the lever of said tie member about the axis of rotation of said pedestal member about said leg member is substantially equal to the lever of said tie member about the axis of rotation of said leg member about said base member.

5. An infant warmer comprising:

a base member having at least two support ends which in use is adapted to lie in a substantially horizontal plane, a columnar support connected to said base member and extending substantially perpendicularly therefrom, an infant support structure connected to said columnar support, said columnar support comprises a cross-sectionally "U" shaped extrusion, said extrusion aligned having the open face thereof facing said infant support structure, and said at least one front panel, each said at least one front panel affixed to said "U" shaped extrusion to enclose a portion of said open face, and a radiant energy source mounted above and adapted to direct radiant energy toward said infant support surface said radiant energy source connected to said columnar support.

6. An infant warmer as claimed in claim 5 wherein said columnar support structure provides mounting means for a plurality of modules.

7. An infant warmer as claimed in claim 6 wherein each said module has a front module panel with operable controls and readable indicia disposed thereon, said front module panel adapted to be affixed to said "U" shaped extrusion to enclose a portion of said open face, with the operative hardware of said module disposed behind said front module panel in the cavity enclosed by said "U" shaped extrusion and said front module panel.

8. An infant warmer as claimed in claim 5 wherein said infant warmer has at least one leg member connected to each said support end of said base member, each said leg member being rotatable about its connection with said base member in a plane having a component substantially perpendicular to said base member, and actuating means operable to rotate each said leg member about its connection with said base member such that the angle between said leg member and said base member may be adjusted thereby adjusting the height of said base member.

9. An infant warmer as claimed in claim 8 wherein said at least one leg member comprises at least two branch segments connected to a support end of said base member.

10. An infant warmer as claimed in claim 9 wherein said at least two branch segments form a substantially "V" shaped leg member wherein the proximal ends of said branch segments are joined together and the distal ends are apart to provide a measure of lateral stability and wherein each distal end is provided with wheel means.

11. An infant wanner as claimed in claim 10 wherein a wheel pedestal member is pivotally connected at one end to the underside of each said branch member adjacent the distal end thereof, with wheel means disposed at its other end, and a tie member is connected at one end to a point on said pedestal member away from the axis of rotation thereof about said leg member and at its other end to a point on said base member, such that the lever of said tie member about the axis of rotation of said pedestal member about said leg member is substantially equal to the lever of said tie member about the axis of rotation of said leg member about said base member.

12. An infant warmer as claimed in claim 8 wherein said actuating means comprise a rotatable control member, and for each said leg member an actuation arm means connected at one end thereof to said rotatable control means at a point thereon away from the axis of rotation, and at the other end thereof to said leg member at a point thereon away from the axis of rotation of said leg member about said base member, so that rotation of said control member causes extension or retraction of said actuation arm relative to the rotation axis of said leg member about said base member, thereby causing rotation of said leg members about their connections with said base member.

13. An infant warmer comprising:
  a base member having at least two support ends which in use is adapted to lie in a substantially horizontal plane,
  a columnar support connected to said base member and extending substantially perpendicularly therefrom,
  an infant support structure connected to said columnar support, and
  a radiant energy source mounted above and adapted to direct radiant energy toward said infant support structure, said radiant energy source connected to said columnar support,
  at least one leg member connected to each said support end of said base member, each said leg member being rotatable about its connection with said base member in a plane having a component substantially perpendicular to said base member, and
  actuating means operable to rotate each said leg member about its connection with said base member such that the angle between said leg member and said base member may be adjusted thereby adjusting, the height of said base member, said actuating means comprising a rotatable control member, and for each said leg member an actuation arm means connected at one end thereof to said rotatable control means at a point thereon away from the axis of rotation, and at the other end thereof to said leg member at a point thereon away from the axis of rotation of said leg member about said base member, so that rotation of said control member causes extension or retraction of said actuation arm relative to the rotation axis of said leg member about said base member, thereby causing rotation of said leg members about their connections with said base member.

14. An infant wanner as claimed in claim 13 wherein the ratio of the lever of said actuation arm means about the axis of rotation of said control member to the lever of said actuation arm means about the axis of rotation of its respective leg member about said base member is constant between said leg members.

15. An infant warmer as claimed in claim 13 wherein the ratio of the lever of said actuation arm means about the axis of rotation of said control member to the lever of said actuation arm means about the axis of rotation of its respective leg member about said base member are constant between said leg members.

16. An infant warmer comprising:
  a base member having at least two support ends which in use is adapted to lie in a substantially horizontal plane,
  a columnar support connected to said base member and extending substantially perpendicularly therefrom,
  an infant support structure connected to said columnar support, and
  a radiant energy source mounted above and adapted to direct radiant energy toward said infant support structure, said radiant energy source connected to said columnar support,
  at least one leg member connected to each said support end of said base member, each said leg member being rotatable about its connection with said base member in a plane having a component substantially perpendicular to said base member,
  actuating means operable to rotate each said leg member about its connection with said base member such that the angle between said leg member and said base member may be adjusted thereby adjusting the height of said base member,
  wherein said at least one leg member comprises at least two branch segments connected to a support end of said base member and said at least two branch segments form a substantially "V" shaped leg member wherein the proximal ends of said branch segments are joined together and the distal ends are apart to provide a measure of lateral stability and wherein each distal end is provided with wheel means.

17. An infant warmer comprising:
  a base member having at least two support ends which in use is adapted to lie in a substantially horizontal plane,
  a columnar support connected to said base member and extending substantially perpendicularly therefrom, an infant support structure connected to said columnar support, and a radiant energy source mounted above and adapted to direct radiant energy toward said infant support structure, said radiant energy source connected to said columnar support, at least one leg member connected to each said support end of said base member, each said leg member being rotatable about its connection with said base member in a plane having a component substantially perpendicular to said base member, actuating means operable to rotate each said leg member about its connection with said base member such that the angle between said leg member and said base member may be adjusted thereby adjusting the height of said base member, wherein said at least one leg member comprises at least two branch segments connected to a support end of said base member, and wherein a wheel pedestal member is pivotally connected at one end to the underside of each said branch member adjacent the distal end thereof, with said wheel means disposed at its other end, and a tie member is connected at one end to a point on said pedestal member away from the axis of rotation thereof about said leg member and at its other end to a point on said base member, such that the lever of said tie member about the axis of rotation of said pedestal member about said leg member is substantially equal to the lever of said tie member about the axis of rotation of said leg member about said base member.

* * * * *

UNITED STATES PATENT AND TRADEMARK OFFICE
CERTIFICATE OF CORRECTION

PATENT NO. : 5,898,817
DATED : April 27, 1999
INVENTOR(S) : Andrew Paul Maxwell Salmon and Christopher Peter Hutchinson It is certified that error appears in the above-identified patent and that said Letters Patent is hereby corrected as shown below:

Title page, item

57 ABSTRACT

Line 4 "source" should be -- surface --

Column 1, Line 53 "die" should be -- the --

Column 2, Line 32 "die" should be -- the --

Column 4, Line 53 "struts, which in turn causes the leg members to " should be -- struts 22, which in turn causes the leg members 7 and 8 to --

Column 4, Lines 61-62 "leg about" should be --leg 7,8 about--.

Column 8, Line 16 "wanner" should be -- warmer --

Signed and Sealed this

Fourteenth Day of December, 1999

Q. TODD DICKINSON

Attest:

Attesting Officer

Acting Commissioner of Patents and Trademarks